US012329376B2

(12) United States Patent
Seykora et al.

(10) Patent No.: US 12,329,376 B2
(45) Date of Patent: *Jun. 17, 2025

(54) BONE CLIP WITH RESILIENT ARM FOR PROXIMAL COMPRESSION

(71) Applicant: Acumed LLC, Hillsboro, OR (US)

(72) Inventors: Andrew W. Seykora, Portland, OR (US); Matthew C. Sucec, Portland, OR (US); Brandon Wedam, North Plains, OR (US)

(73) Assignee: Acumed LLC, Hillsboro, OR (US)

( * ) Notice: Subject to any disclaimer, the term of this patent is extended or adjusted under 35 U.S.C. 154(b) by 546 days.

This patent is subject to a terminal disclaimer.

(21) Appl. No.: 17/688,349

(22) Filed: Mar. 7, 2022

(65) Prior Publication Data

US 2022/0183680 A1 Jun. 16, 2022

Related U.S. Application Data

(63) Continuation of application No. 16/250,869, filed on Jan. 17, 2019, now Pat. No. 11,278,277.

(51) Int. Cl.
*A61B 17/064* (2006.01)
*A61B 17/00* (2006.01)
(Continued)

(52) U.S. Cl.
CPC ...... *A61B 17/0642* (2013.01); *A61B 17/0682* (2013.01); *A61B 2017/00867* (2013.01);
(Continued)

(58) Field of Classification Search
CPC . A61B 17/0642; A61B 17/0682; A61B 17/10; A61B 17/8004; A61B 2017/0641; A61B 2017/0645
See application file for complete search history.

(56) References Cited

U.S. PATENT DOCUMENTS

| 4,848,328 A | 7/1989 | Laboureau et al. |
| 5,089,009 A | 2/1992 | Green |

(Continued)

FOREIGN PATENT DOCUMENTS

| JP | 2016-214869 A | 12/2016 |
| JP | 2017-520343 A | 7/2017 |

(Continued)

OTHER PUBLICATIONS

Communication corresponding to related European Patent Application No. 20742024.1 dated May 29, 2024, 5 pages.

(Continued)

*Primary Examiner* — Kevin T Truong
*Assistant Examiner* — Diana Jones
(74) *Attorney, Agent, or Firm* — Knobbe, Martens, Olson & Bear, LLP (57) ABSTRACT

Devices and methods for stabilizing bone. The devices and methods may provide a more balanced proximal and distal compression when stabilizing bone. An exemplary device may comprise a staple member including a bridge connecting a first leg to a second leg. The device also may comprise a resilient arm elongated between a fixed end and a free end, and projecting from the first leg and/or from an end region of the bridge adjoining the first leg. At least a portion of the resilient arm intermediate the fixed and free ends may be inwardly adjacent and spaced from an upper region of the first leg.

19 Claims, 8 Drawing Sheets

(51) Int. Cl.
*A61B 17/068* (2006.01)
*A61B 17/10* (2006.01)
*A61B 17/80* (2006.01)

(52) U.S. Cl.
CPC ............... *A61B 2017/0641* (2013.01); *A61B 2017/0645* (2013.01); *A61B 17/10* (2013.01); *A61B 17/8004* (2013.01)

(56) References Cited

U.S. PATENT DOCUMENTS

| | | | |
|---|---|---|---|
| 9,486,212 | B2 | 11/2016 | Miller et al. |
| 10,105,134 | B2 | 10/2018 | Biedermann et al. |
| 2009/0264923 | A1 | 10/2009 | Sater |
| 2010/0292715 | A1 | 11/2010 | Nering et al. |
| 2013/0030437 | A1 | 1/2013 | Fox |
| 2013/0153627 | A1* | 6/2013 | Euteneuer ............ A61F 2/0811 227/175.1 |
| 2013/0240598 | A1 | 9/2013 | Euteneuer et al. |
| 2017/0202552 | A1 | 7/2017 | Coleman et al. |
| 2018/0353172 | A1 | 12/2018 | Hartdegen et al. |
| 2019/0046182 | A1 | 2/2019 | Krumme |

FOREIGN PATENT DOCUMENTS

| | | |
|---|---|---|
| JP | 2017-192747 A | 10/2017 |
| JP | 2018-526123 A | 9/2018 |
| WO | 2017003743 A1 | 1/2017 |
| WO | 2017139315 A1 | 8/2017 |

OTHER PUBLICATIONS

International Search Report corresponding to related International Patent Application No. PCT/US2020/013568 mailed Apr. 21, 2020, 2 pages.
International Written Opinion corresponding to related International Patent Application No. PCT/US2020/013568 mailed Apr. 21, 2020, 5 pages.
International Preliminary Report corresponding to related International Patent Application No. PCT/US2020/013568 mailed Jul. 29, 2021, 7 pages.
Japanese First Office Action corresponding to related Japanese Patent Application No. 2021-541479 mailed Aug. 21, 2023, 23 pages.
Extended European Search Report corresponding to related European Patent Application No. 20742024.1 mailed Sep. 22, 2022, 9 pages.
Japanese Decision of Rejection corresponding to related Japanese Patent Application No. 2021-541479 mailed Dec. 4, 2023, 17 pages.

* cited by examiner

BONE CLIP WITH RESILIENT ARM FOR PROXIMAL COMPRESSION

PRIORITY CLAIM

The present application is a continuation of U.S. application Ser. No. 16/250,869, filed Jan. 17, 2019, now U.S. Pat. No. 11,278,277, issued Mar. 22, 2022, which is herein incorporated by reference in its entirety.

INTRODUCTION

A bone clip, also called a bone staple, is a fastener for stabilizing bone. The clip may be installed in one or more bones to span a discontinuity in the bone(s), such as a fracture, a cut, or an anatomical joint. Once installed, the clip applies compression across the discontinuity, to encourage healing and/or fusion.

Figure 1:
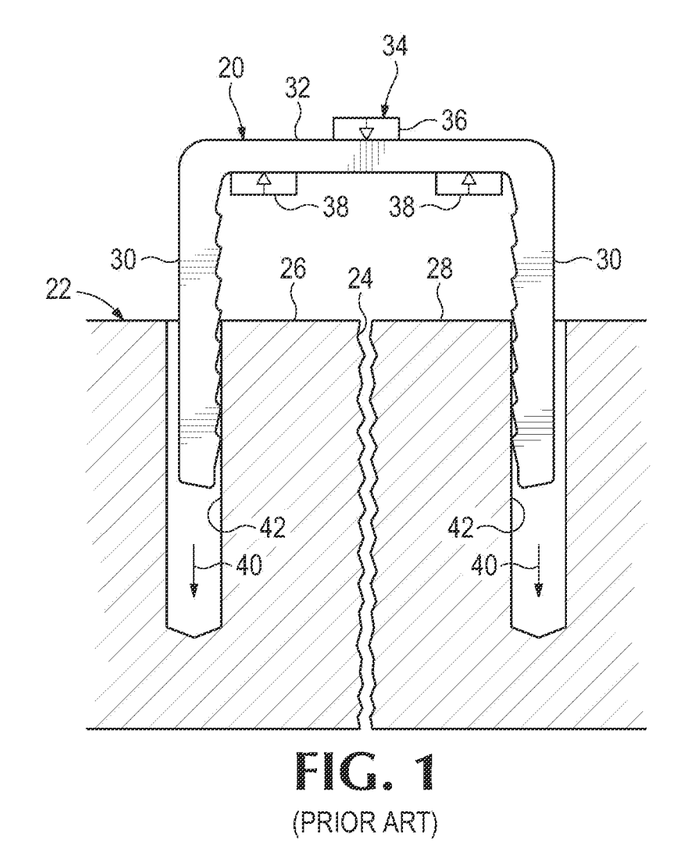
FIG. 1 is a fragmentary, sectional view of a fractured bone taken during installation of a bone clip representing the prior art, with legs of the bone clip being advanced into pre-drilled holes in the bone, and with the bone clip held in an elastically deformed, stressed configuration by an exemplary insertion tool.
Figure 2:
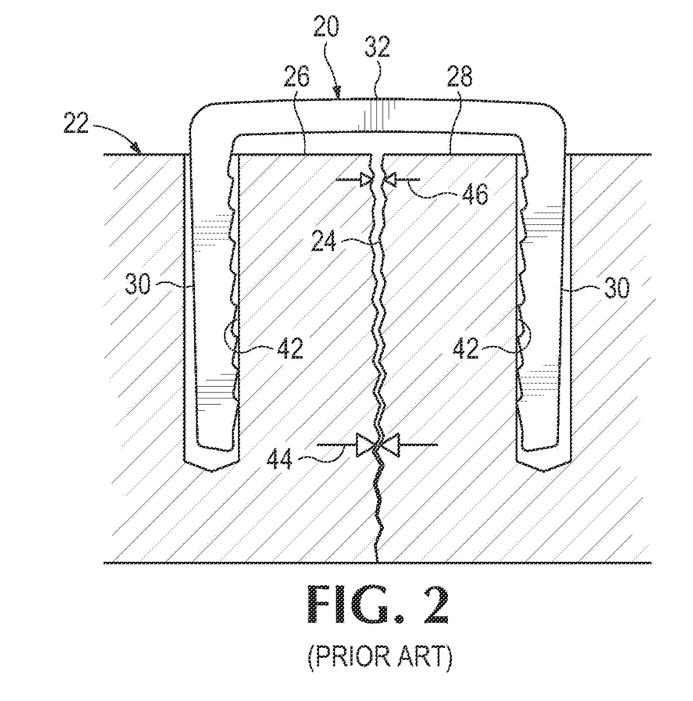
FIG. 2 is a fragmentary, sectional view of the fractured bone of FIG. 1 taken after installation of the bone clip has been completed and showing uneven compression along the fracture of the bone.

An exemplary bone clip 20 representing the prior art is shown in FIGS. 1 and 2, respectively during and after insertion into a bone 22. The bone has a fracture 24 that creates bone fragments 26, 28. Clip 20 has a pair of serrated legs 30 connected to one another with a bridge 32. Legs 30 extend along convergent paths from bridge 32 when clip 20 is in an undeformed, relaxed configuration (not shown). Clip 20 is composed of an elastically deformable material, which allows the clip to be placed and held temporarily in a stressed configuration with an insertion tool 34. For example, tool 34 may have upper and lower jaws 36, 38 that apply a bending moment to bridge 32, which reorients legs 30 to be substantially parallel to another in the stressed configuration shown in FIG. 1. Tool 34 maintains clip 20 in the stressed configuration while legs 30 are being inserted, indicated at 40, into parallel, pre-drilled holes 42 in fragments 26, 28.

FIG. 2 shows clip 20 after legs 30 have been fully inserted into holes 42, and insertion tool 34 has been removed. Clip 20 acts as a spring clamp, with legs 30 as jaws. The legs urge bone fragments 26, 28 toward one another as energy stored in the stressed configuration of clip 20 is released, to apply compression across fracture 24. However, this design does not apply compression uniformly along fracture 24. Instead, as shown in FIG. 2, the amount of compression is related to the distance from bridge 32, with distal compression 44 between the free ends of legs 30 being significantly greater than proximal compression 46. This difference in compressive force is indicated by force arrows of different size and a residual gap proximally at the fracture site. An improved bone clip is needed.

SUMMARY

The present disclosure provides devices and methods for stabilizing bone. The devices and methods may provide a more balanced proximal and distal compression when stabilizing bone. An exemplary device may comprise a staple member including a bridge connecting a first leg to a second leg. The device also may comprise a resilient arm elongated between a fixed end and a free end, and projecting from the first leg and/or from an end region of the bridge adjoining the first leg. At least a portion of the resilient arm intermediate the fixed and free ends may be inwardly adjacent and spaced from an upper region of the first leg.

DETAILED DESCRIPTION

The present disclosure provides devices and methods for stabilizing bone. The devices and methods may provide a more balanced proximal and distal compression when stabilizing bone. An exemplary device may comprise a staple member including a bridge connecting a first leg to a second leg. The device also may comprise a resilient arm elongated between a fixed end and a free end, and projecting from the first leg and/or from an end region of the bridge adjoining the first leg. At least a portion of the resilient arm intermediate the fixed and free ends may be inwardly adjacent and spaced from an upper region of the first leg.

Another exemplary device for stabilizing bone is provided. The device may comprise a staple member including a bridge connecting a first leg to a second leg. The device also may comprise an arm inwardly adjacent and pivotally connected to an upper region of the first leg. The arm may be firmly attached to a lower region of the first leg.

An exemplary method for stabilizing bone with the device is provided. In the method, a first hole and a second hole are drilled in bone. The first leg and the arm of the device may be inserted into the first hole, and the second leg of the device may be inserted into the second hole.

Further aspects of the present disclosure are described in the following sections: (I) overview of bone clips for proximal compression, (II) methods of stabilizing bone with bone clips, and (III) examples.

I. OVERVIEW OF BONE CLIPS FOR PROXIMAL COMPRESSION

Figures 3, 3A, 4:
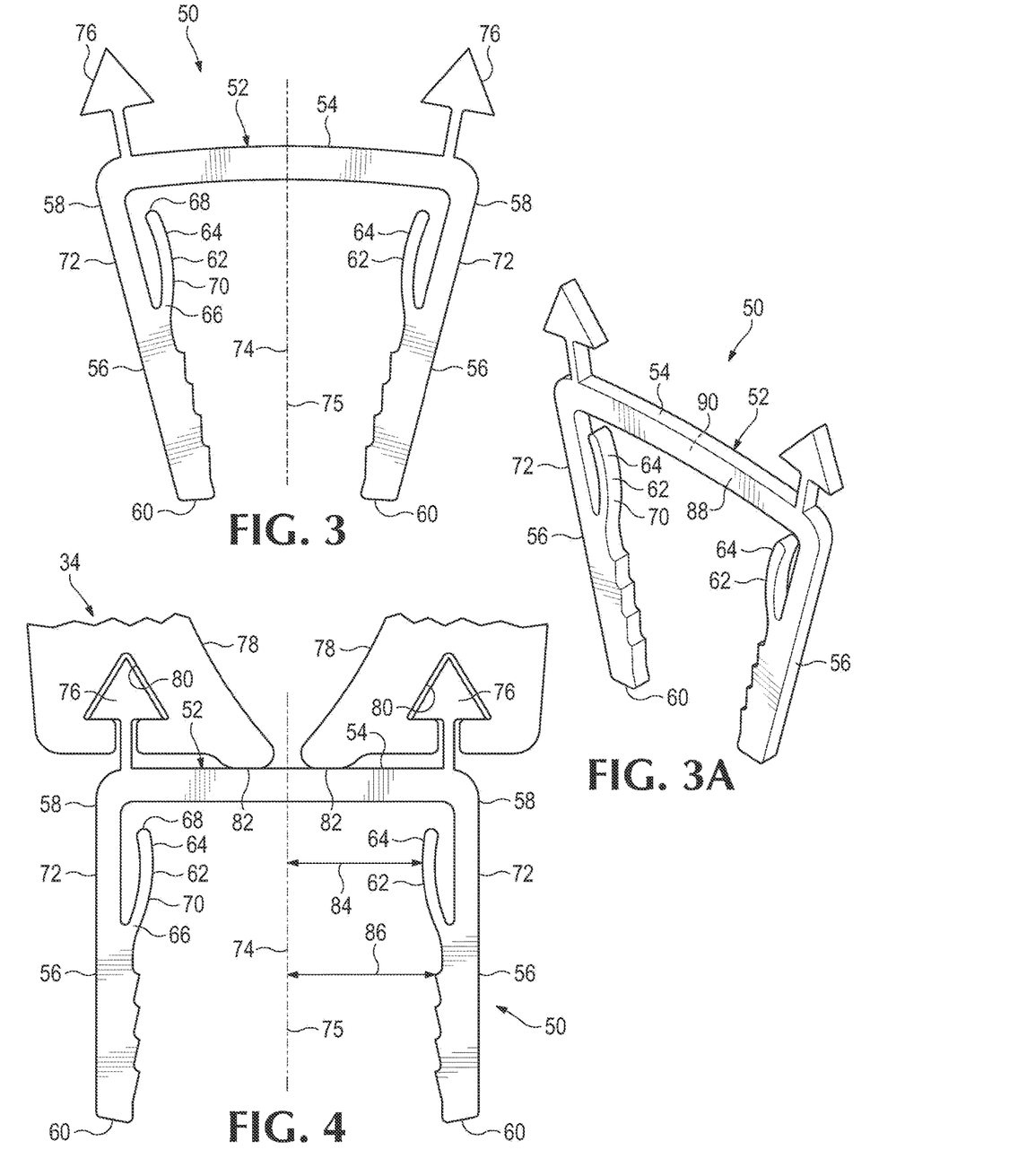
FIG. 3 is a front view of an exemplary bone clip in a relaxed configuration, with the bone clip having a pair of resilient arms projecting from respective legs and configured to provide more balanced compression of bone.
FIG. 3A is an isometric view of the bone clip of FIG. 3.
FIG. 4 is a front view of the bone clip of FIG. 3 being held in an elastically deformed configuration by an exemplary insertion tool (shown as fragmentary).

This section provides an overview of bone clips that provide proximal compression using at least one spring member and/or arm, as exemplified by bone clip 50; see FIGS. 3, 3A, and 4.

Bone clip 50 is shown in a relaxed configuration in FIGS. 3 and 3A, and in a stressed configuration in FIG. 4. Clip 50 includes a staple member 52 having a bridge 54 joined to and interconnecting a pair of legs 56. Each leg 56 has an upper end 58 (interchangeably called a proximal end) that forms a junction with bridge 54, and a lower end 60 (interchangeably called a distal end) that is farthest from bridge 54. The terms "upper" and "lower," and "proximal" and "distal," are defined by relative proximity to bridge 54, with upper and proximal being closer to the bridge than lower and distal. The terms "inner" and "outer" are respectively closer to and farther from a central plane and/or central axis, as defined below. In other embodiments, bone clip 50 may have at least three or at least four legs 56 (e.g., see Example 2 of Section III).

A spring member 62 may be associated with at least one leg 56, or respective spring members 62 may be associated with at least two legs, such as each leg 56 as in the depicted embodiment. More specifically, each spring member 62 may project from one of legs 56 and/or from an end region of bridge 54 adjoining the leg. In the depicted embodiment, each spring member 62 is an arm 64 that projects proximally from leg 56 and has a distal fixed end 66 and a proximal free end 68. Arm 64 may be described as a resilient arm (i.e., the arm is elastically deformable, which allows the arm to function as a spring, such as a cantilever spring). In other embodiments, fixed end 66 is proximal and free end 68 is distal, both ends of spring member 62 are fixed ends, and/or spring member 62 includes a pair of resilient arms 64 associated with one of legs 56 (see Example 1 of Section III). In other embodiments, the bone clip includes a plurality of discrete pieces that are pivotably connected to one another (see Example 3 of Section III).

Spring member 62 and/or arm 64 may have any suitable properties. At least a portion 70 of spring member 62 and/or arm 64 intermediate its ends may be located inwardly adjacent and spaced from an upper region 72 of associated leg 56. The term "inward" as used herein means at least generally toward a different leg(s) 56 of bone clip 50, and/or at least generally toward a central plane 74 (and/or a central axis 75) that intersects bridge 54 and is centered between legs 56. The terms "inner" and "outer" are respectively closer to and farther from central plane 74 or axis 75. For example, in the depicted embodiment, each leg 56 has a serrated inner side and a smooth outer side.

Portion 70 (and/or free end 68) may be spaced from upper region 72 of associated leg 56 by any suitable distance, such as less than about 25%, 20%, or 15% of the maximum distance between legs 56, and/or more than about 2%, 3%, 4% or 5% of this maximum distance. A larger spacing may be preferable in some cases, in order to maintain compression dynamically as bone is resorbed from the interface between bone fragments and/or bones.

The spring member and/or arm may be elongated between ends thereof to define a longitudinal axis, which may be linear or curved, among others. The curvature may, for example, be convex with respect to central plane 74 and/or axis 75, as in the depicted embodiment. A curved longitudinal axis may be preferred in some cases, as it may offer the spring member and/or arm two distinct spring constants, namely, a first spring constant for closing the gap, if any, between free end 68 and upper region 72, and a second spring constant for reducing the curvature, if any, of the spring member and/or arm.

Legs 56 may extend convergently from bridge 54 when bone clip 50 is in a relaxed configuration, as shown in FIGS. 3 and 3A. In other words, upper ends 58 of legs 56 may be significantly farther from one another than lower ends 60 are to one another. Each leg may form any suitable angle with a respective plane that is parallel to central plane 74 (and/or with a respective axis that is parallel to central axis 75), such as at least about 5 or 10 degrees, and/or about 5-25 degrees or 10-20 degrees, among others. Legs 56 may form angles of the same size with the planes and/or axes.

Legs 56 may be substantially parallel to one another, as in FIG. 4, when bone clip 50 is being held in a stressed configuration by an insertion tool 34, before or during insertion into bone. Insertion tool 34 may engage only bridge 54 of bone clip 50 (as in FIG. 1) to apply deforming stress. In other embodiments, insertion tool 34 may engage bridge 54 and legs 56, or legs 56 alone, of the bone clip.

In some embodiments, bone clip 50 may have one or more protrusions, such as tabs 76, to facilitate operative engagement of insertion tool 34 with bone clip 50. Each protrusion may project from any suitable position of staple member 52, such as the top side of bridge 54, as shown here, longitudinally from bridge 54 at an end thereof, the front and/or back side of bridge 54, the bottom side of bridge 54, and/or one of legs 56. Each protrusion may be configured to be detached from staple member 52, such as by breaking off or cutting the protrusion from the staple member, or the protrusion may be sized and positioned to remain attached to staple member 52 after bone clip 50 has been implanted in a subject.

Insertion tool 34 may deform bridge 54 by applying a bending moment to staple member 52. Bridge 54 may be bowed upward (or straight) in the relaxed configuration of staple member 52, as shown in FIG. 3, and may be less curved and/or bowed downward in the stressed configuration of staple member 52, as shown in FIG. 4.

Insertion tool 34 may create the bending moment by applying downward stress centrally along bridge 54, and upward stress closer to the ends of bridge 54. For example, in the depicted embodiment, insertion tool 34 has a pair of limbs 78 with respective cutouts 80 that mate with tabs 76. Limbs 78 then are rotated toward one another, which causes a toe 82 of each limb 78 to press downward on a central region of bridge 54, while a wall of each cutout 80 pulls upward on one of tabs 76. Limbs 78 then may be locked to one another, to maintain bone clip 50 in the stressed configuration of FIG. 4 until legs 56 have been inserted into bone.

Each arm 64 may be closer than its associated leg 56 to central plane 74 and/or axis 75 when bone clip 50 is in the stressed configuration of FIG. 4. In other words, a minimum distance 84 between arm 64 and plane 74 and/or axis 75 may be less than a minimum distance 86 between leg 56 and plane 74 and/or axis 75. Insertion of bone clip 50 into bone, while the bone clip is held in the stressed configuration of FIG. 4, may increase distance 84 by elastically deforming at least one arm 64, as described further below.

The bone clips of the present disclosure may have any suitable construction and composition. Each bone clip may be formed as only one piece (i.e., a unitary construction), as in FIG. 3, or may include two or more discrete pieces that are movably connected to one another (e.g., see Example 3 of Section III). Any combination of bridge 54, legs 56, spring member(s) 62 (and/or arm(s) 64), and tabs 76 (if any) may be formed integrally with one another. The bone clip may be formed of any suitable biocompatible material, such as metal (stainless steel, titanium, titanium alloy, cobalt chrome, magnesium, magnesium alloy, etc.), polymer, or the like. In some embodiments, the bone clip may be composed of nickel titanium, also known as Nitinol, which is an alloy of nickel and titanium, generally in roughly equal amounts. Nickel titanium may be described as a shape memory alloy.

Bone clip 50 may have a uniform thickness measured between a front side 88 and a back side 90 (see FIG. 3A). Sides 88, 90 may be substantially planar surfaces that are parallel to one another. Accordingly, the bone clip may be manufactured by cutting the clip from a flat plate. The thickness of bone clip 50 may be greater than, about the same as, or less than, the average width of bridge 54 and/or each leg 56 (measured in a plane defined the bridge and legs). For example, the thickness may be at least about 25% of the average width of the bridge and/or each leg.

Further aspects of bone clip 50 that may be suitable are described elsewhere herein, such as in Sections II and III.

II. METHODS OF STABILIZING BONE WITH BONE CLIPS

This section describes exemplary methods of stabilizing bone with the bone clips of the present disclosure, as exemplified with bone clip 50 of FIGS. 3, 3A, and 4 having two legs 56 each associated with a resilient arm 64; see FIGS. 4-9. The steps described here can be performed in any suitable order and combination using any of the bone clips of the present disclosure.

Figure 5:
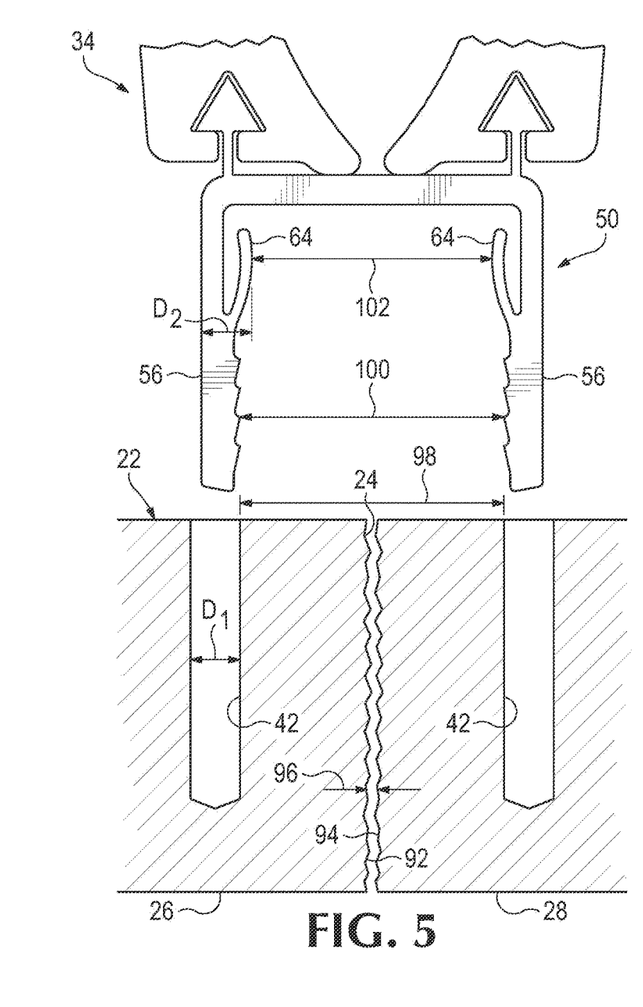
FIGS. 5-8 are a series of sectional, fragmentary views of the fractured bone of FIG. 1 each taken during (FIGS. 5-7) or after (FIG. 8) installation of the bone clip of FIGS. 3, 3A, and 4 using the insertion tool of FIG. 4.

Bone to be stabilized may be selected. The bone may be a single bone 22 or at least a pair of adjacent bones (e.g., to be fused to one another). If a single bone, the bone may have a fracture 24 (as shown in FIG. 5), a cut (for an osteotomy), a structural weakness, or the like. Exemplary bones that may be suitable include long bones of the arm (humerus, ulna, and/or radius), bones of the hand (carpals, metacarpals, and/or phalanges), long bones of the leg (femur, tibia, and/or fibula), bones of the foot (talus, calcaneus, tarsals, metatarsals, and/or phalanges), the pelvis, ribs, the sternum, vertebrae, clavicles, scapulas, or the like. The bone may be stabilized temporarily by the bone clip, only during a surgical procedure, or more permanently for any suitable amount of time after the bone clip has been implanted in a subject. Accordingly, the bone clip may be used for fracture fixation, osteotomy fixation, fusion of bones of an anatomical joint, temporary reduction, or the like.

A bone clip may be selected for stabilizing the bone. The bone clip may have two legs, or three or more legs. The size of the bone clip may be chosen according to the size of bone to be stabilized and the magnitude of loads to be exerted on the bone once stabilized.

Holes 42 may be drilled in the selected bone. A separate hole 42 may be drilled to receive each leg 56 of bone clip 50. Each hole may be slightly deeper than the length of leg 56 to be received. The holes may be positioned such that a discontinuity in the selected bone (e.g., fracture 24) is intermediate a pair of legs 56 of the clip. Each hole 42 may be drilled generally normal to the local exterior surface of the selected bone, and the holes may be drilled parallel to one another. The holes may be drilled after pieces of bone are aligned and surfaces thereof (e.g., fracture or cut surfaces 92, 94) are approximated, although a small gap 96 between fragments 26, 28 may be present. Holes 42 may be spaced from one another such that a minimum distance 98 between the holes substantially matches a minimum distance 100 between legs 56. A minimum distance 102 between arms 64 is generally less than distance 98 (and distance 100). Each hole 42 may have a diameter $D_1$, and bone clip 50 may define a collective, relaxed maximum width $D_2$ of the corresponding leg 56 and arm 64, measured in a plane defined by the bone clip. Generally, $D_1 \geq D_2$.

Figure 6:
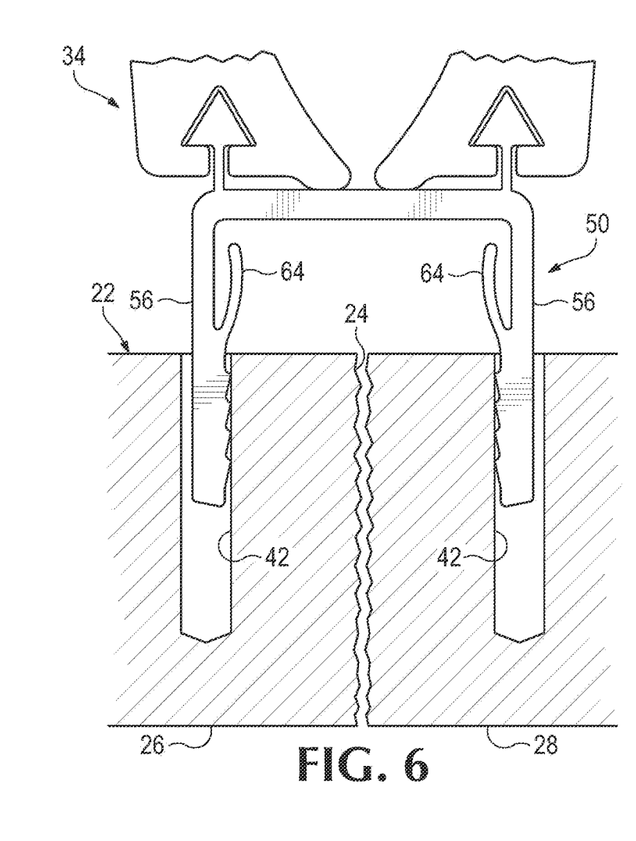
Figure 7:
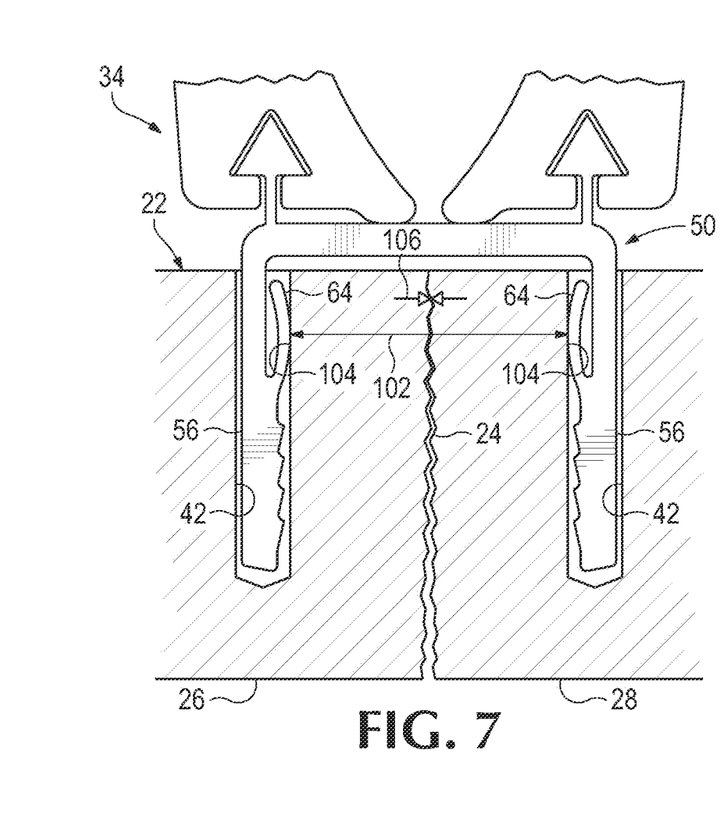

Bone clip 50 may be deformed to a stressed configuration with insertion tool 34. The insertion tool may hold the bone clip in the stressed configuration until legs 56 of bone clip 50 are substantially fully inserted into respective holes 42, as shown in FIGS. 6 and 7. As shown in FIG. 7, the process of insertion may cause arms 64 to move farther apart from one another by deformation (to increase distance 102 relative to FIG. 5). Since a small gap 96 between bone fragments or bones may be present at the start of insertion, bone fragments 26, 28 also may be moved closer together (to decrease distance 98 proximally (see FIG. 5)). This movement may be produced by force exerted on the near sides 104 of holes 42 by arms 64 as the proximal portions of legs 56 and their adjacent arms 64 are inserted into holes 42 (see FIG. 7). The gap, if any, between bone fragments 26, 28 may be closed only proximally, in response to proximal compression 106 applied by arms 64. The arms may be compressed toward their associated legs 56 by contact with near side 104 of each hole 42. As a result, the collective width corresponding to $D_2$ may be reduced (also see FIG. 5).

Figure 8:
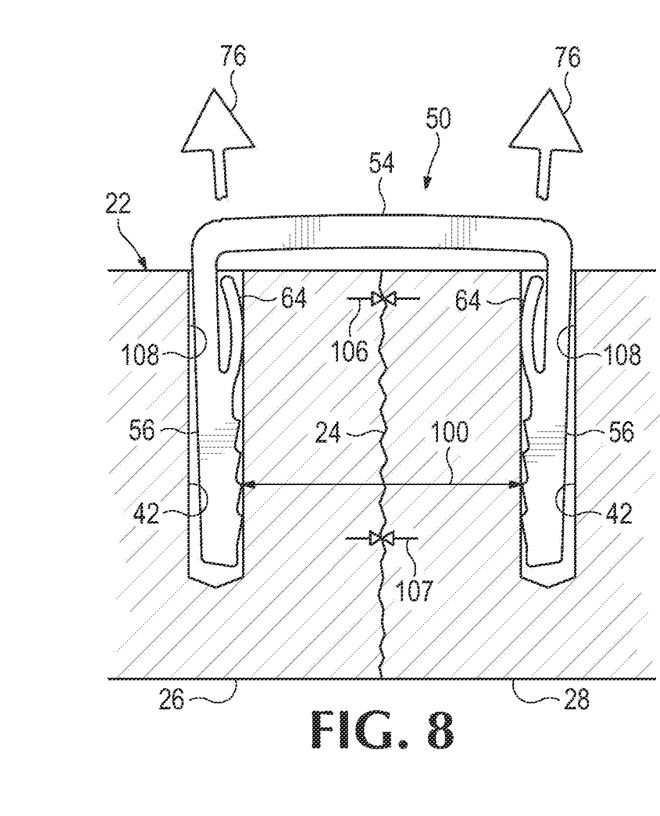

FIG. 8 shows bone clip 50 in a fully installed configuration. Insertion tool 34 has been removed, and tabs 76 have been detached from bridge 54. Legs 56 have moved closer to one another, to decrease distance 100, which results in distal compression 107. Compression may be more uniform along fracture 24 than with bone clips of the prior art (e.g., see FIGS. 1 and 2). Furthermore, bone clip 50 can continue to apply proximal and distal compression 106, 107 if bone resorption occurs around fracture 24 during healing. This resorption may further decrease distance 98 (also see FIG. 5), as arms 64 expand inward from legs 56 to apply proximal compression dynamically. (This expansion increases the collective width measured between the outer side of leg 56 and the inner side of corresponding arm 64.) The outer sides of legs 56 do not contact the far sides 108 of holes 42, even if arms 64 return to their relaxed configurations, when $D_1 > D_2$.

Figure 9:
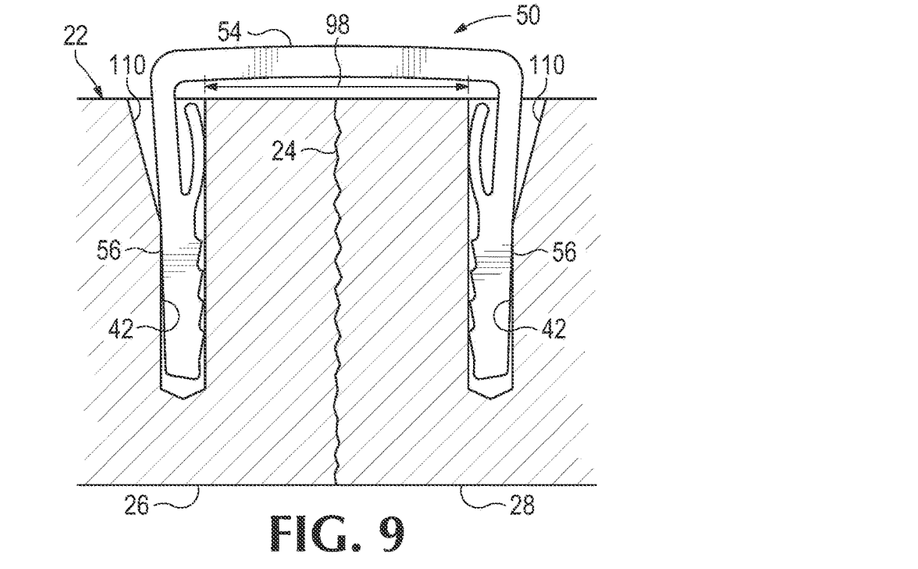
FIG. 9 is a fragmentary, sectional view of a fractured bone taken after installation of the bone clip of FIGS. 3, 3A, and 4 in different holes than in FIGS. 5-8.

FIG. 9 shows bone clip 50 installed in holes 42 that have been widened proximally, but selectively at far sides thereof, indicated at 110. This widening may be performed with a punch, before or after bone clip 50 has been installed. The use of a punch or similar tool allows distance 98 to remain the same, while increasing the diameter of hole 42 proximally to accommodate a greater amount of bone resorption (and thus a greater distance of travel of the bone fragments toward one another). Accordingly, a smaller total volume of bone can be removed relative to drilling wider holes 42 at the outset.

III. EXAMPLES

This section describes selected embodiments of bone clips for stabilizing bone and methods of using the bone clips to stabilize bone. Any of the features of the devices and methods described in this section may be combined with one another and with any of the features described elsewhere in the present disclosure, in any suitable combination.

These embodiments are intended for illustration and should not limit the entire scope of the present disclosure.

Example 1

Spring Member Configurations

This example describes exemplary alternative spring member configurations for incorporation into bone clip 50 of FIGS. 3, 3A, and 4-9; see FIGS. 10-14. Only one leg 56 and an end region of bridge 54 are shown for each embodiment. Each other leg 56 of the clip may (or may not) be associated with a spring member, optionally similar to what is shown.

Figure 10:
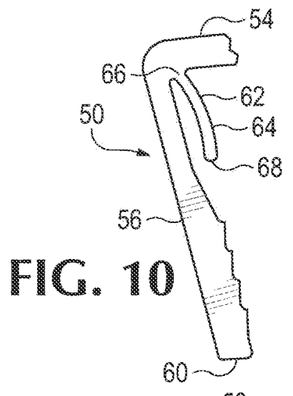
FIG. 10 is a fragmentary front view of an exemplary bone clip having a resilient arm that projects away from the bridge of the bone clip.

FIG. 10 shows a bone clip 50 having a spring member 62 in the form of a resilient arm 64 projecting distally from bridge 54. A fixed end 66 of arm 64 is located at the junction between bridge 54 and leg 56, and a free end 68 of the arm is located distally therefrom, closer to lower end 60 of leg 56.

Figure 11:
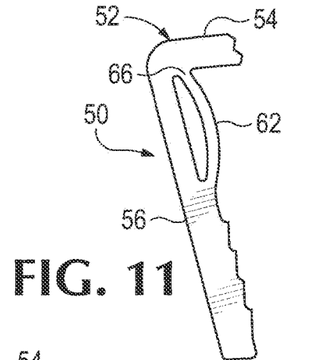
FIG. 11 is a fragmentary front view of an exemplary bone clip having a spring member that is fixed at both ends.

FIG. 11 shows a bone clip 50 having a spring member 62 with no free end. Instead, both ends are fixed to staple member 52.

Figure 12:
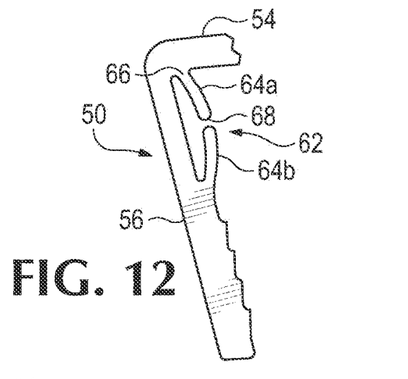
FIG. 12 is a fragmentary front view of an exemplary bone clip having a pair of resilient arms associated with the same leg.

FIG. 12 shows a bone clip 50 having a spring member 62 formed by a pair of resilient arms 64a, 64b. Each arm 64a, 64b has a fixed end 66 and a free end 68. Arm 64a projects distally from bridge 54, and arm 64b projects proximally from leg 56.

Figure 13:
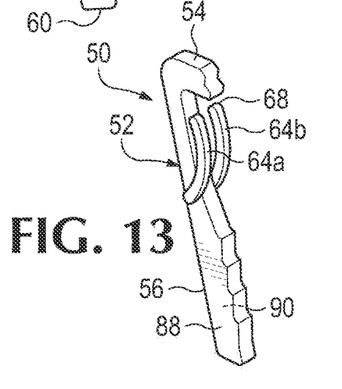
FIG. 13 is a fragmentary isometric view of another exemplary bone clip having a pair of resilient arms associated with the same leg.

FIG. 13 shows a bone clip 50 having a pair of resilient arms 64a, 64b each extending proximally from leg 56 to a free end 68 that is closer to bridge 54. The arms are attached to front side 88 and back side 90, respectively, of leg 56, and may be offset transversely from staple member 52.

Figure 14:
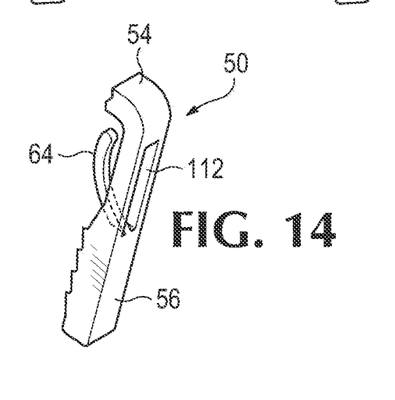
FIG. 14 is a fragmentary isometric view of an exemplary bone clip having a resilient arm that projects from a slot defined by an associated leg.

FIG. 14 shows a bone clip 50 having a resilient arm 64 projecting proximally from a slot 112 defined by a leg 56. Slot 112 may be sized to permit at least part of arm 64 to move into the slot as the arm is deformed.

Example 2

Bone Clips with at Least Three Legs

Figure 15:
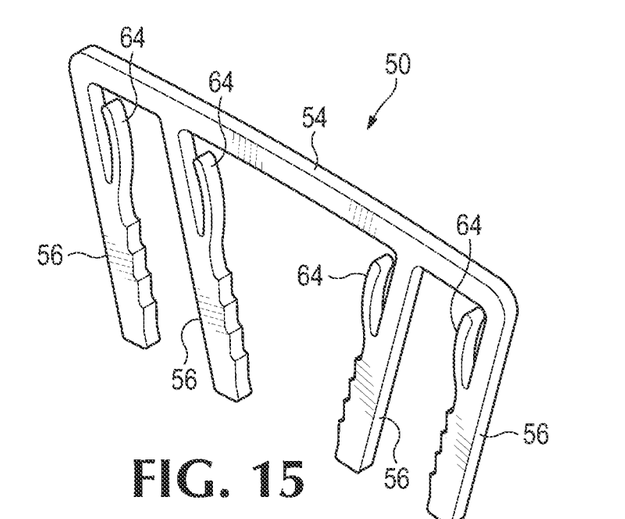
FIG. 15 is an isometric view of an exemplary bone clip having four coplanar legs each associated with a resilient arm.
Figure 16:
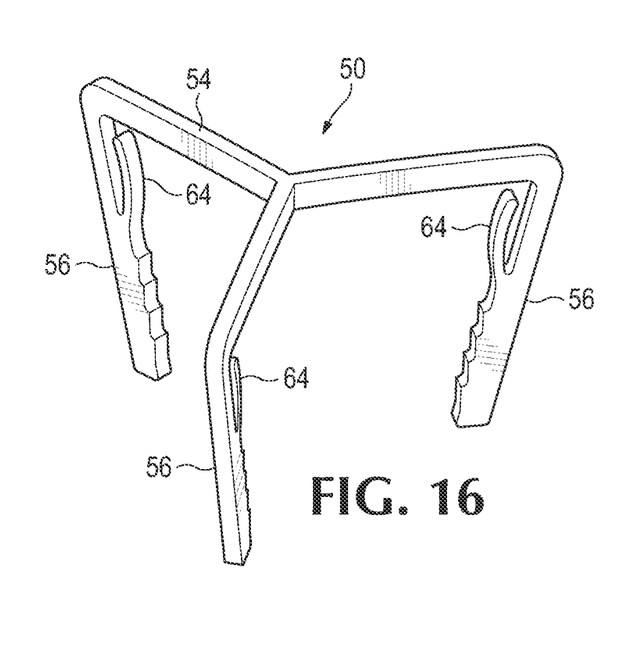
FIG. 16 is an isometric view of an exemplary bone clip having a triangular arrangement of three legs each associated with a resilient arm.
Figure 17:
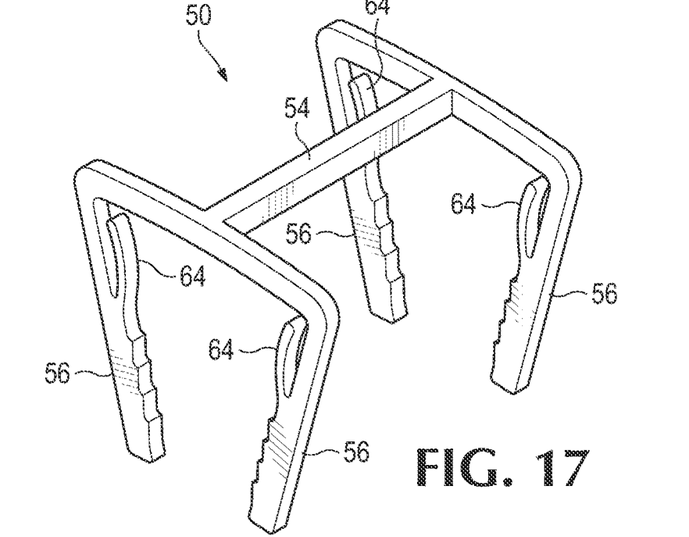
FIG. 17 is an isometric view of an exemplary bone clip having a rectangular arrangement of four legs each associated with a resilient arm.

This example describes exemplary bone clips 50 having at least three legs and including a spring member and/or resilient arm to apply proximal compression to bone; see FIGS. 15-17.

FIG. 15 shows a bone clip 50 having four coplanar legs 56 each associated with a respective resilient arm 64. In other embodiments, only a subset of legs 56 are associated with a resilient arm 64.

FIG. 16 shows a bone clip 50 having a triangular arrangement of three legs 56 each associated with a resilient arm 64. In other embodiments, only a subset of legs 56 are associated with a resilient arm 64.

FIG. 17 shows a bone clip 50 having a rectangular arrangement of four legs 56 each associated with a resilient arm 64. In other embodiments, only a subset of legs 56 are associated with a resilient arm 64.

Example 3

Bone Clip with Pivotally Connected Members

Figure 18:
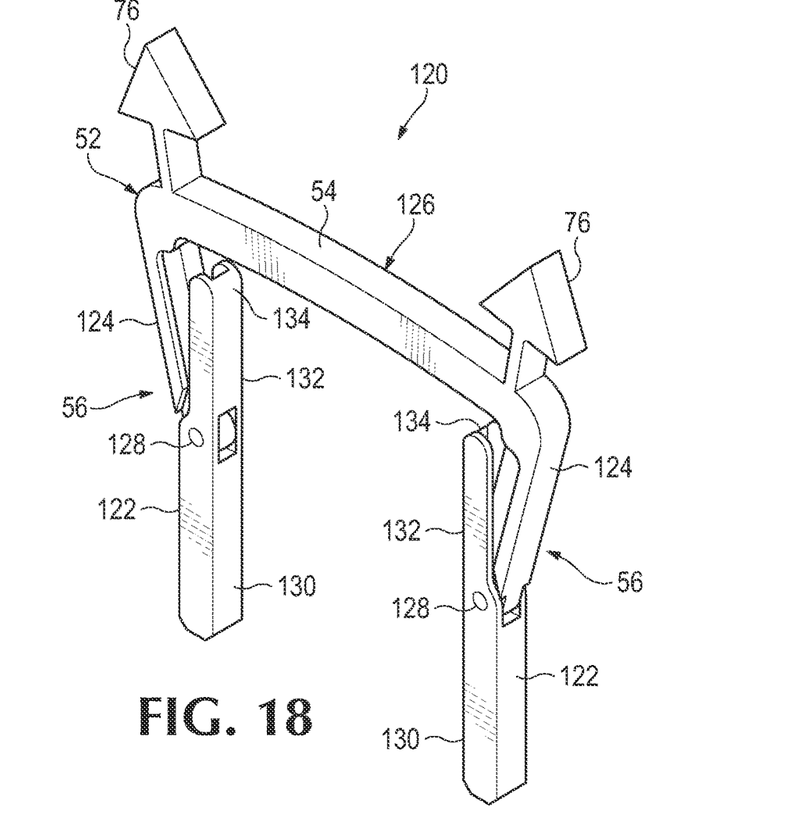
FIG. 18 is an isometric view of an exemplary multi-piece bone clip having a pair of hinged elongate members.

This example describes an exemplary bone clip 120 including at least one pivotally connected elongate member 122; see FIG. 18.

Bone clip 120 includes a staple member 52 having a bridge 54 connecting a pair of legs 56 to one another. Bridge 54 and a pair of upper leg regions 124 are formed by a body 126, which may be only one piece. A respective elongate member 122 is pivotally connected at a pivotable joint 128 to a distal end of each upper leg region 124. Elongate member 122 forms a lower leg region 130 of one of legs 56 and also forms an arm 132. However, arm 132 may be substantially less deformable than arm 64 of bone clip 50. Arm 132 may be firmly attached to lower leg region 130 (e.g., formed integrally with the lower leg region), and may extend proximally from pivotable joint 128 to a proximal end 134.

Bone clip 120 may be installed as described above in Section II for bone clip 50. However, pivotal motion of each elongate member 122, rather than elastic deformation of an arm with respect to an associated leg, provides balanced proximal and distal compression.

Example 4

Bone Clip with Resilient Arms and a Slanted or Stepped Bridge

This example describes exemplary bone clips 50 having a slanted bridge 54 (FIG. 19) or a stepped bridge 54 (FIG. 20) connecting a pair of legs 56 to one another. The bone clips are shown in a stressed configuration (e.g., similar to FIG. 4) with legs 56 parallel to one another, but, for simplification, in the absence of an insertion tool to produce/maintain the stressed configuration. Each bone clip 50 may have a respective spring member 62 and/or resilient arm 64 associated with at least one leg 56 (or each leg 56 as shown). The bone clips of this example may have any suitable combination of features described in the present disclosure.

Figure 19:
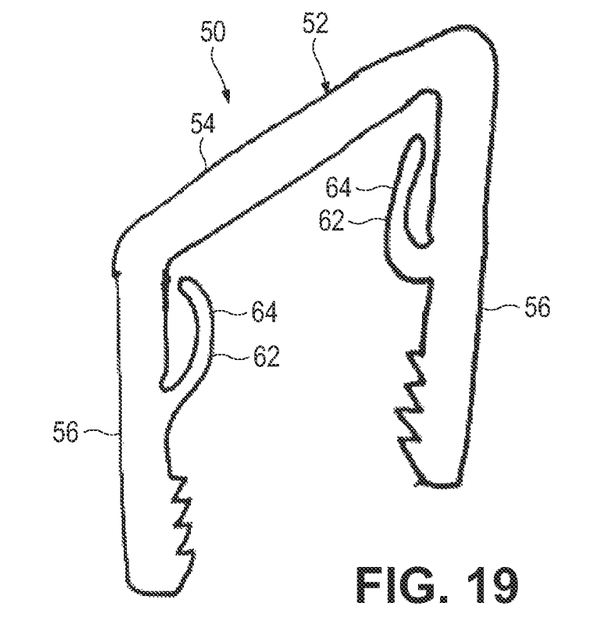
FIG. 19 is a front view of an exemplary bone clip arranged in a stressed configuration (i.e., with its legs parallel to one another) and having a pair of resilient arms and a slanted bridge.

FIG. 19 shows bridge 54 forming an angle of less than 90 degrees with a leg 56 at one end and an angle of greater than 90 degrees with the other leg. The angles may add up to about 180 degrees when the bone clip is in the stressed configuration, as shown here. The smaller angle may be less than about 85, 80, 75, 70, 65, or 60 degrees, among others, and/or greater than about 30, 40, 45, 50, or 60 degrees, among others.

Figure 20:
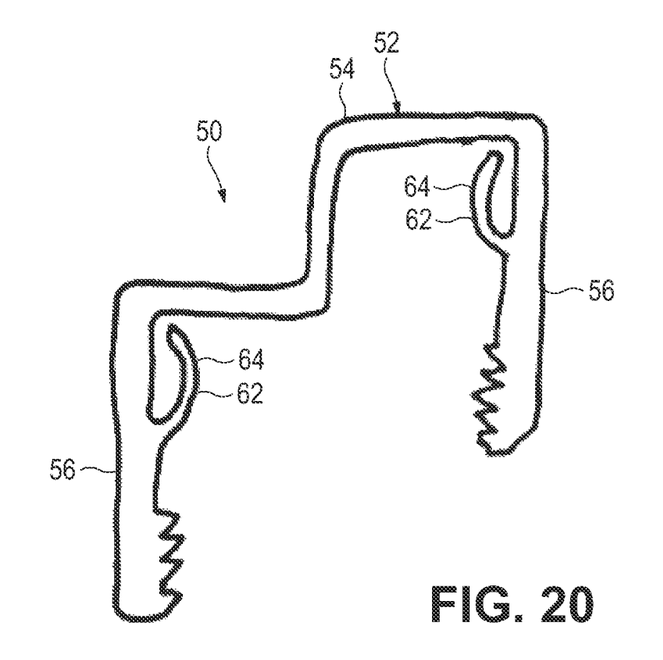
FIG. 20 is a front view of an exemplary bone clip arranged in a stressed configuration (i.e., with its legs parallel to one another) and having a pair of resilient arms and a stepped bridge.

FIG. 20 shows bridge 54 forming an angle of about 90 degrees with each leg 56. However, the bridge bends abruptly intermediate the ends thereof, to form a step, which offsets the legs relative to another parallel to a central axis of the clip.

Example 5

Selected Embodiments

This example describes selected aspects of the present disclosure as a series of indexed paragraphs.

Paragraph 1. A device for stabilizing bone, comprising: (a) a staple member including a bridge connecting a first leg to a second leg; and (b) a resilient arm elongated between a fixed end and a free end, and projecting from the first leg and/or from an end region of the bridge adjoining the first leg, wherein at least a portion of the resilient arm intermediate the fixed and free ends is inwardly adjacent and spaced from an upper region of the first leg.

Paragraph 2. The device of paragraph 1, wherein the staple member has a stressed configuration in which the first and second legs are parallel to one another, and in which a minimum distance between the resilient arm (in its relaxed configuration) and a plane centered between the first leg and the second leg is less than a minimum distance between the first leg and the plane.

Paragraph 3. The device of paragraph 2, wherein the resilient arm and the first leg collectively have a maximum width, and wherein the resilient arm is configured to be elastically deformable to reduce the maximum width while the staple member remains in the stressed configuration.

Paragraph 4. The device of any of paragraphs 1 to 3, wherein a separation distance between a portion of the resilient arm and the upper region of the first leg is configured to decrease by elastic deformation of the resilient arm when the device is installed in bone.

Paragraph 5. The device of any of paragraphs 1 to 4, wherein the fixed end of the resilient arm is farther than the free end from the bridge.

Paragraph 6. The device of any of paragraphs 1 to 5, wherein the staple member has a relaxed configuration, and wherein the first and second legs extend convergently from the bridge along their respective longitudinal axes in the relaxed configuration.

Paragraph 7. The device of any of paragraphs 1 to 6, wherein the device has a relaxed configuration, wherein a line intersects the fixed end and the free end of the resilient arm, and wherein the line is within about 10, 20, 25, or 30 degrees of parallel to a longitudinal axis of the first leg when the device is in the relaxed configuration.

Paragraph 8. The device of any of paragraphs 1 to 7, wherein one of the fixed and free ends of the resilient arm is an upper end and the other of the fixed and free ends of the resilient arm is a lower end, and wherein the first leg and the resilient arm have a collective width measured from an outer side of the first leg to an inner side of the resilient arm, and wherein the collective width tapers away from the bridge near the lower end of the resilient arm when the device is in a relaxed configuration.

Paragraph 9. The device of any of paragraphs 1 to 8, wherein the resilient arm is spaced from the staple member along an entire length of the resilient arm, except at the fixed end, when the device is in a relaxed configuration.

Paragraph 10. The device of any of paragraphs 1 to 9, wherein the resilient arm has a curved longitudinal axis.

Paragraph 11. The device of any of paragraphs 1 to 10, wherein the resilient arm is a first resilient arm, further comprising a second resilient arm projecting from the second leg and/or from an end region of the bridge adjoining the second leg.

Paragraph 12. The device of paragraph 11, wherein the staple member has a stressed configuration in which the first and second legs are parallel to one another, and in which a minimum distance between the first resilient arm and the second resilient arm is less than a minimum distance between the first leg and the second leg.

Paragraph 13. The device of paragraph 12, wherein the first resilient arm and the second resilient arm are configured to deform elastically to increase the minimum distance between the first resilient arm and the second resilient arm while the staple member remains in the stressed configuration.

Paragraph 14. The device of any of paragraphs 1 to 13, wherein the device is composed of a nickel titanium alloy.

Paragraph 15. The device of any of paragraphs 1 to 14, wherein the staple member defines a plane, and wherein the staple member and the resilient arm have the same thickness as one another orthogonal to the plane.

Paragraph 16. The device of any of paragraphs 1 to 15, wherein the staple member and the resilient arm are formed integrally with one another. Paragraph 17. The device of any of paragraphs 1 to 16, wherein the device is only one discrete piece.

Paragraph 18. The device of any of paragraphs 1 to 17, wherein the staple member has at least three legs connected to one another by the bridge.

Paragraph 19. The device of any of paragraphs 1 to 18, wherein the device is configured to be used for cortical and/or cancellous bone.

Paragraph 20. The device of any of paragraphs 1 to 19, (i) wherein each leg is located in a hole formed in a bone or bone fragment, and/or (ii) wherein a central axis is centered between the legs, and wherein upper ends of the legs are offset relative to one another parallel to the central axis, and/or wherein the bridge is slanted and/or stepped to produce an offset of the upper ends of the legs relative to one another parallel to the central axis.

Paragraph 21. A method of stabilizing bone using the device of any of paragraphs 1 to 20, the method comprising: (i) drilling a first hole and a second hole in bone; and (ii) inserting the first leg and the resilient arm into the first hole, and the second leg into the second hole.

Paragraph 22. The method of paragraph 21, wherein the step of inserting elastically deforms the resilient arm outward.

Paragraph 23. The method of paragraph 21 or 22, wherein the step of inserting applies proximal compression to the bone.

Paragraph 24. The method of paragraph 23, wherein the proximal compression is applied in part by contact between the resilient arm and the bone at the first hole.

Paragraph 25. The method of paragraph 23 or 24, wherein the device has a pair of resilient arms, and wherein the proximal compression is applied to the bone by the pair of resilient arms at the first and second holes.

Paragraph 26. The method of any of paragraphs 21 to 25, further comprising a step of applying distal compression to the bone via contact between the first leg and the first hole and between the second leg and the second hole.

Paragraph 27. The method of paragraph 26, wherein the step of inserting is performed while the staple member is held in a stressed configuration with an insertion tool, wherein the distal ends of the first and second legs are farther apart from one another in the stressed configuration relative to a relaxed configuration of the staple member, and wherein the step of applying distal compression includes a step of releasing the staple member from the insertion tool.

Paragraph 28. The method of any of paragraphs 21 to 27, wherein the first and second holes are formed in the same bone, and wherein the same bone has a fracture or a cut intermediate the first and second holes.

Paragraph 29. The method of any of paragraphs 21 to 28, wherein the step of inserting includes a step of moving a portion of the resilient arm closer to the first leg, and/or a step of moving bone fragments or different bones closer to one another.

Paragraph 30. The method of any of paragraphs 21 to 29, wherein the first and second holes have respective near sides that are closer to one another than central axes of the holes, and wherein the step of inserting places the resilient arm in contact with the near side of the first hole.

Paragraph 31. The method of paragraph 30, wherein the resilient arm is a first resilient arm, wherein the device has a second resilient arm associated with the second leg, and wherein the step of inserting places the second arm in contact with the near side of the second hole.

Paragraph 32. The method of any of paragraphs 21 to 31, wherein the first leg and the resilient arm have a collective width when the device is in a relaxed configuration, and wherein the step of inserting reduces the collective width.

Paragraph 33. A device for stabilizing bone, comprising: (a) a staple member including a bridge connecting a first leg to a second leg; and (b) an arm inwardly adjacent and pivotally connected to an upper region of the first leg; wherein the arm is firmly attached to a lower region of the first leg.

Paragraph 34. The device of paragraph 33, wherein the first leg has a pivotable joint formed intermediate a proximal end and a distal end of the first leg, and wherein the arm and the lower region of the first leg are formed by an elongate member that is rotatable as a unit with respect to the upper region of the first leg via the pivotable joint.

Paragraph 35. The device of paragraph 33 or 34, wherein the arm and the lower region of the first leg are formed integrally with one another.

Paragraph 36. The device of any of paragraphs 33 to 35, wherein the arm is a first arm and the elongate member is a first elongate member, wherein a second elongate member forms a second arm and a lower region of the second leg and is pivotable with respect to an upper region of the second leg.

Paragraph 37. The device of any of paragraphs 33 to 36, wherein the bridge is formed integrally with the upper region of the first leg and with an upper region of the second leg, and wherein a respective elongate member is pivotally connected to a distal end of the upper region of the first leg and the upper region of the second leg.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

The invention claimed is:

1. A device for stabilizing a first bone part and a second bone part, comprising:
   a staple member including a bridge connecting a first leg to a second leg;
   a first resilient arm projecting from at least one of the first leg, the bridge, and a corner joining the first leg and the bridge, wherein the first resilient arm is configured to elastically deform towards the first leg; and
   a second resilient arm projecting from at least one of the second leg, the bridge, and a corner joining the second leg and the bridge, wherein the second resilient arm is configured to elastically deform towards the second leg,
   wherein the first resilient arm is positioned with respect to the first leg, and the second resilient arm is positioned with respect to the second leg, such that, while the device is being installed in the first and second bone parts, the first resilient arm and the second resilient arm apply a compressive force to the first and second bone parts thereby compressing a gap between the first and second bone parts.

2. The device of claim 1, wherein there is an absence of material between a portion of the first resilient arm and the first leg.

3. The device of claim 1, wherein the first resilient arm is elongated between a first end and a second end, wherein the first end of the first resilient arm projects from one of the first leg, the bridge, and the corner joining the first leg and the bridge, and wherein the second end of the first resilient arm is free from connection with any other component.

4. The device of claim 1, wherein the first resilient arm is elongated between a first end and a second end, wherein the first end of the first resilient arm projects from the first leg, and wherein the second end of the first resilient arm projects from the bridge or the corner joining the first leg and the bridge.

5. The device of claim 1, further comprising a third resilient arm projecting from at least one of the first leg, the bridge, and the corner joining the first leg and the bridge, wherein the third resilient arm is configured to elastically deform towards the first leg.

6. The device of claim 5, wherein the first resilient arm and the third resilient arm both project from one of the first leg, the bridge, and the corner joining the first leg and the bridge.

7. The device of claim 5, wherein one of the first resilient arm and the third resilient arm projects from the first leg and the other of the first resilient arm and the third resilient arm projects from the bridge or the corner joining the first leg and the bridge.

8. The device of claim 1, wherein at least one of the first leg and the second leg includes a slot, and wherein the slot is sized to receive a portion of the first or second resilient arm when the first or second resilient arm is deformed towards the first leg or the second leg respectively.

9. The device of claim 1, wherein the staple member has at least three legs connected to one another by the bridge, wherein the at least three legs include the first leg, the second leg, and a third leg.

10. The device of claim 9, wherein each of the at least three legs is in a same plane.

11. The device of claim 9, wherein one or more of the at least three legs is in a different plane than the remaining legs of the at least three legs.

12. The device of claim 1, wherein the bridge is elastically deformable such that the staple member has a stressed configuration and a relaxed configured, wherein the first and second legs are parallel to one another when the staple member is in the stressed configuration, and wherein the first and second legs are non-parallel to one another when the staple member is in the relaxed configuration.

13. The device of claim 12, wherein when the staple member is in the stressed configuration, the device is symmetrical about an axis equally spaced between the first and second legs.

14. The device of claim 12, wherein when the staple member is in the stressed configuration, the device is asymmetrical about an axis equally spaced between the first and second legs.

15. The device of claim 1, wherein the first leg and the first resilient arm are formed integrally with one another.

16. The device of claim 1, wherein the staple member defines a plane, and wherein the staple member and the first resilient arm have the same thickness as one another orthogonal to the plane.

17. A method for stabilizing a first bone part and a second bone part, the method comprising:
    obtaining a device including:
        a staple member including a bridge connecting a first leg to a second leg;
        a first resilient arm projecting from at least one of the first leg, the bridge, and a corner joining the first leg and the bridge, wherein the first resilient arm is configured to elastically deform towards the first leg; and
        a second resilient arm projecting from at least one of the second leg, the bridge, and a corner joining the second leg and the bridge, wherein the second resilient arm is configured to elastically deform towards the second leg;
    drilling a first hole in the first bone part;
    drilling a second hole in the second bone part; and
    inserting the first leg into the first hole and the second leg into the second hole, wherein the first resilient arm is positioned with respect to the first leg, and the second resilient arm is positioned with respect to the second leg, such that, while the first and second legs are being inserted into the first and second holes, the first resilient arm and the second resilient arm apply a compressive force to the first and second bone parts thereby compressing a gap between the first and second bone parts.

18. The method of claim 17, wherein a single bone includes the first bone part and the second bone part such that the gap is a fracture, cut, or structural weakness in the single bone between the first bone part and the second bone part.

19. The method of claim 17, wherein the first bone part is a first discrete bone and the second bone part is a second discrete bone.

\* \* \* \* \*